(12) United States Patent
Marshall

(10) Patent No.: US 11,504,465 B2
(45) Date of Patent: *Nov. 22, 2022

(54) INLINE PUMP WITH REAR ATTACHABLE SYRINGE

(71) Applicant: FLEX FLUIDICS, LLC, Las Vegas, NV (US)

(72) Inventor: Michael Marshall, Las Vegas, NV (US)

(73) Assignee: FLEX FLUIDICS, LLC, Las Vegas, NV (US)

( * ) Notice: Subject to any disclaimer, the term of this patent is extended or adjusted under 35 U.S.C. 154(b) by 171 days.

This patent is subject to a terminal disclaimer.

(21) Appl. No.: 16/946,257

(22) Filed: Jun. 12, 2020

(65) Prior Publication Data

US 2020/0306427 A1  Oct. 1, 2020

Related U.S. Application Data

(63) Continuation of application No. 15/847,651, filed on Dec. 19, 2017, now Pat. No. 10,695,470, which is a continuation of application No. 14/504,756, filed on Oct. 2, 2014, now Pat. No. 9,849,221.

(60) Provisional application No. 61/887,078, filed on Oct. 4, 2013.

(51) Int. Cl.
| *A61M 1/00* | (2006.01) |
| *A61M 5/145* | (2006.01) |
| *F04B 11/00* | (2006.01) |
| *A61M 39/10* | (2006.01) |

(52) U.S. Cl.
CPC ............ *A61M 1/81* (2021.05); *A61M 5/1452* (2013.01); *F04B 11/0091* (2013.01); *A61M 1/0058* (2013.01); *A61M 2005/14506* (2013.01); *A61M 2039/1077* (2013.01)

(58) Field of Classification Search
CPC .. A61M 5/24; A61M 5/31551; A61M 5/3158; A61M 5/31585; A61M 5/172; A61M 5/1452; A61M 5/142; A61M 5/14216; G06F 19/3468; Y10S 128/12
See application file for complete search history.

(56) References Cited

U.S. PATENT DOCUMENTS

| 2,156,023 A * | 4/1939 | McKay | A61M 5/204 604/184 |
| 2,627,270 A * | 2/1953 | Bronislaw | A61M 5/1452 604/257 |
| 2,671,449 A * | 3/1954 | Morris | A61M 5/24 604/193 |

(Continued)

*Primary Examiner* — Scott J Medway
(74) *Attorney, Agent, or Firm* — Innovation Capital Law Group, LLP; Vic Lin

(57) ABSTRACT

Inline pumps with rear attachable syringes include a pump and a syringe with each designed so that the pump syringe system may be easily coupled and decoupled in the field. An end mount block on the pump has a slot shaped to accept a similarly shaped plunger button and plunger rod on the syringe. A user aligns the plunger button of the syringe next to the slot on the mount block of the pump, and slides the plunger button and rod into the inner cavity of the pump. Both the pump and the syringe have threaded couplers which securely couple the pump to the syringe by rotating the couplers with respect to each other.

20 Claims, 7 Drawing Sheets

(56) References Cited

U.S. PATENT DOCUMENTS

| | | | | |
|---|---|---|---|---|
| 2,687,725 A | * | 8/1954 | Hein, Jr. | A61M 5/30 604/70 |
| 2,826,195 A | * | 3/1958 | Ashkenaz | A61M 5/24 604/193 |
| 3,390,815 A | * | 7/1968 | Zdenek | G01F 11/02 222/137 |
| 3,425,416 A | * | 2/1969 | Loughry | A61M 5/488 92/84 |
| 3,768,472 A | * | 10/1973 | Hodosh | A61M 5/20 604/143 |
| 3,841,331 A | * | 10/1974 | Wilder | A61M 1/80 604/152 |
| 3,993,064 A | * | 11/1976 | McCarthy | A01F 7/70 604/294 |
| 4,250,887 A | * | 2/1981 | Dardik | A61B 6/481 600/432 |
| 4,327,724 A | * | 5/1982 | Birk | G01F 11/029 604/152 |
| 4,335,834 A | * | 6/1982 | Zepkin | B05C 17/0103 222/327 |
| 4,370,982 A | * | 2/1983 | Reilly | A61M 25/10184 604/920 |
| 4,651,738 A | * | 3/1987 | Demer | A61M 25/10188 604/920 |
| 4,655,749 A | * | 4/1987 | Fischione | A61M 25/10184 604/184 |
| 4,808,165 A | * | 2/1989 | Carr | A61M 25/1018 604/920 |
| 4,966,601 A | * | 10/1990 | Draenert | A61B 17/8827 606/92 |
| 4,995,432 A | * | 2/1991 | Tervamaki | B67D 7/66 417/477.13 |
| 5,015,233 A | * | 5/1991 | McGough | A61M 5/142 604/920 |
| 5,034,003 A | * | 7/1991 | Denance | A61M 5/20 604/117 |
| 5,160,327 A | * | 11/1992 | Stines | A61M 27/008 604/920 |
| 5,219,099 A | * | 6/1993 | Spence | B01L 3/0227 422/926 |
| 5,413,255 A | * | 5/1995 | Dent | A61D 7/00 222/387 |
| 5,450,988 A | * | 9/1995 | Jerdee | F16H 25/2025 74/424.89 |
| 5,505,697 A | * | 4/1996 | McKinnon, Jr. | A61M 5/30 604/152 |
| 5,647,853 A | * | 7/1997 | Feldmann | A61M 5/16854 604/154 |
| 5,692,642 A | * | 12/1997 | Brattesani | A61C 5/62 221/199 |
| 5,808,203 A | * | 9/1998 | Nolan, Jr. | A61M 5/14546 604/67 |
| 6,582,405 B2 | * | 6/2003 | Kawagishi | A61M 5/315 604/131 |
| 6,958,053 B1 | * | 10/2005 | Reilly | A61M 5/14546 604/154 |
| 7,699,815 B2 | * | 4/2010 | Langley | A61M 5/14244 604/209 |
| 8,235,256 B2 | * | 8/2012 | Green | B05C 17/015 222/324 |
| 9,192,727 B2 | * | 11/2015 | Møller | A61M 5/31553 |
| 9,533,093 B2 | * | 1/2017 | Schafer | A61M 5/1452 |
| 9,795,535 B2 | * | 10/2017 | Aguerre | A61M 5/1452 |
| 9,943,651 B2 | * | 4/2018 | Deutsch | A61M 16/044 |
| 2002/0016567 A1 | * | 2/2002 | Hochman | A61M 5/1456 128/DIG. 13 |
| 2002/0183616 A1 | * | 12/2002 | Toews | A61M 5/007 128/920 |
| 2007/0270744 A1 | * | 11/2007 | Dacquay | A61F 9/0017 604/114 |
| 2008/0287873 A1 | * | 11/2008 | Liberatore | G16H 20/17 604/131 |
| 2010/0268168 A1 | * | 10/2010 | Cole | A61M 5/1483 604/207 |
| 2012/0088206 A1 | * | 4/2012 | Tanaka | A61M 5/24 433/90 |
| 2012/0123257 A1 | * | 5/2012 | Stokes, Jr. | A61M 5/1782 600/432 |
| 2012/0271197 A1 | * | 10/2012 | Castle | A61B 5/150946 600/583 |
| 2014/0228763 A1 | * | 8/2014 | Kondoh | A61M 5/172 604/154 |

* cited by examiner

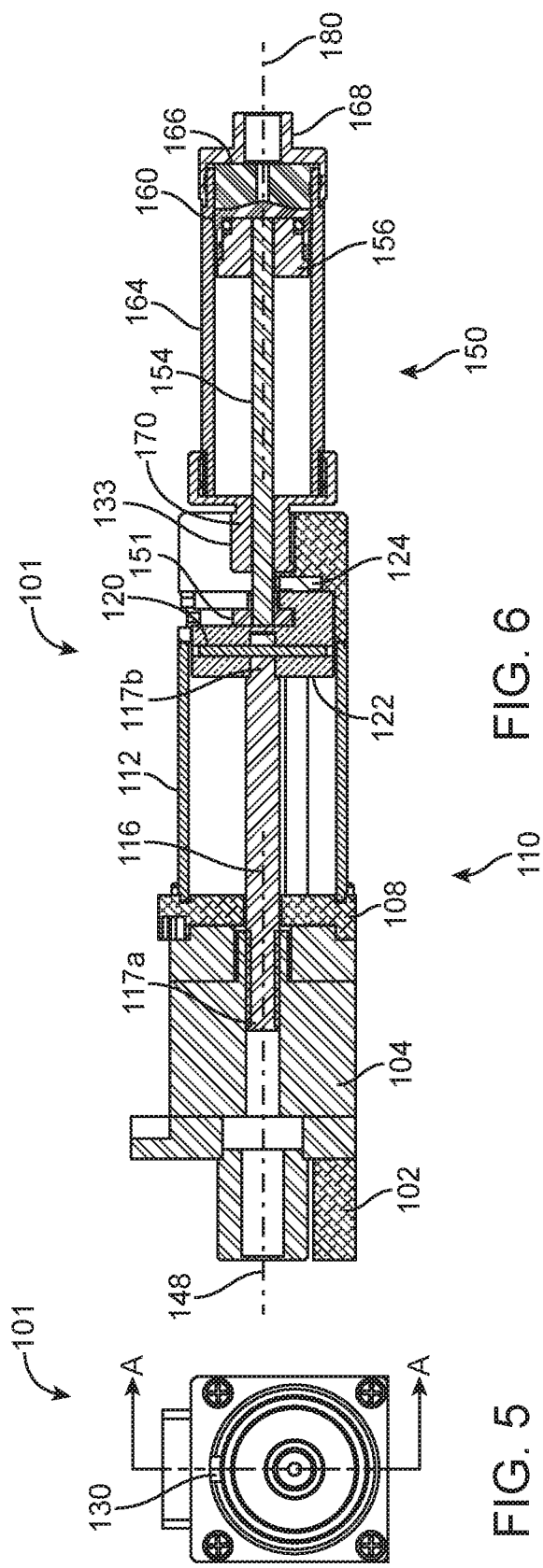

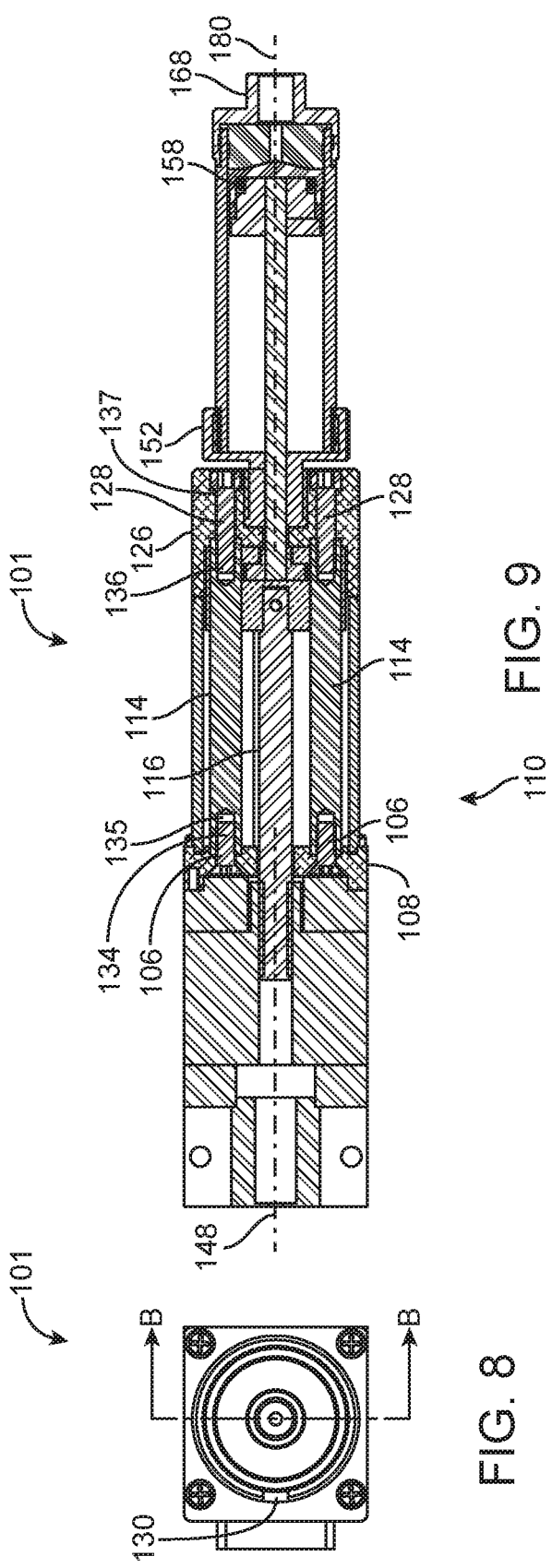

INLINE PUMP WITH REAR ATTACHABLE SYRINGE

RELATED APPLICATION INFORMATION

The present application claims priority under 35 U.S.C. Section 119(e) to U.S. Provisional Patent Application Ser. No. 61/887,078 filed Oct. 4, 2013 entitled "INLINE PUMP REAR ATTACHABLE SYRINGE", and to U.S. Non-provisional patent application Ser. No. 14/504,756 filed Oct. 2, 2014, and to U.S. Non-provisional patent application Ser. No. 15/847,651 filed Dec. 19, 2017, the disclosures of which are incorporated herein by reference in their entirety.

BACKGROUND OF THE INVENTION

Field of the Invention

The present invention relates in general to pumps. More particularly, the invention is directed to inline syringe pumps.

Description of the Related Art

Syringe pumps may be employed in life sciences applications and may be found in clinical or analytic equipment. Repairing conventional syringe pumps in the field may be expensive and difficult. Moreover, users may wish to change the volume of the syringe, or repair the pump syringes without requiring outside repair servicing.

Accordingly, a need exists to improve syringe pump systems.

SUMMARY OF THE INVENTION

In the first aspect, a syringe pump system is disclosed. The syringe pump system comprises a pump and a syringe. The pump comprises a linear actuator, a shaft having a shaft longitudinal axis, the shaft having a first and a second end, the first end coupled to the linear actuator, and a cylindrical syringe connector coupled to the second end of the shaft. The syringe comprises a plunger rod, the plunger rod having a plunger longitudinal axis, and a plunger button coupled to the plunger rod, the plunger button configured to detachably mate with the syringe connector.

In a first preferred embodiment, the shaft longitudinal axis is coincident with the plunger longitudinal axis. The plunger button preferably comprises a cylindrical disc radially extending away from the plunger rod, and the cylindrical syringe connector centered about the shaft longitudinal axis, the syringe connector having a T-slot formed the outer radial surface of the syringe connector forming a channel on the adjacent flat surface of the syringe connector extending to the radial center of the syringe connector. The T-slot on the cylindrical syringe connector is preferably configured to receive the plunger button and the plunger rod and align the plunger longitudinal axis coincident with the shaft longitudinal axis. The pump preferably further comprises a mount block at an end of the pump, the mount block having a mount block T-slot formed the outer radial surface of the mount block and forming a channel on the outer flat surface of the mount block extending to the radial center of the mount block, where the mount block is configured to align with the syringe connector and receive the plunger button during assembly. The mount block preferably further comprises a mount block threaded coupler, and the syringe further comprises a syringe threaded coupler. The mount block threaded coupler is preferably configured to receive and mate with the syringe threaded coupler to detachably connect the syringe to the pump.

The pump preferably further comprises an adapter plate mounted to the linear actuator, the adapter plate having an adapter plate through hole coincident with the shaft longitudinal axis, and a plurality of guide stand-offs, each guide stand-off coupled to the adapter plate, passing through guide through holes on the syringe connector, and coupled to the mounting plate, where the guide stand-offs prevent the syringe connector from rotating about the shaft. The pump preferably further comprises a micro-switch placed on the mount block, the micro-switch configured to detect the immediate presence of the syringe connector. The linear actuator preferably comprises a stepper motor. The syringe preferably comprises a glass syringe. The pump preferably further comprises a sleeve, where the sleeve surrounds the cylindrical syringe connector.

In a second aspect, a pump for a syringe pump system is disclosed. The pump comprises a linear actuator, a shaft having a shaft longitudinal axis, the shaft having a first and a second end, the first end coupled to the linear actuator, and a cylindrical syringe connector coupled to the second end of the shaft, cylindrical syringe connector configured to detachably mate with a plunger button of a syringe, and position the shaft longitudinal axis coincident with a plunger longitudinal axis of a plunger rod.

In a second preferred embodiment, the cylindrical syringe connector is centered about the shaft longitudinal axis, the syringe connector having a T-slot formed the outer radial surface of the syringe connector forming a channel on the adjacent flat surface of the syringe connector extending to the radial center of the syringe connector. The cylindrical syringe connector is preferably configured to receive the plunger button and the plunger rod of a syringe and align the plunger longitudinal axis coincident with the shaft longitudinal axis. The pump preferably further comprises a mount block at an end of the pump, the mount block having a mount block T-slot formed the outer radial surface of the mount block and forming a channel on the outer flat surface of the mount block extending to the radial center of the mount block, where the mount block is configured to align with the syringe connector and receive the plunger button during assembly. The mount block preferably further comprises a mount block threaded coupler.

The pump preferably further comprises an adapter plate mounted to the linear actuator, the adapter plate having an adapter plate through hole coincident with the shaft longitudinal axis, and a plurality of guide stand-offs, each guide stand-off coupled to the adapter plate, passing through guide through holes on the syringe connector, and coupled to the mounting plate, where the guide stand-offs prevent the syringe connector from rotating about the shaft. The pump preferably further comprises a micro-switch placed on the mount block, the micro-switch configured to detect the immediate presence of the syringe connector. The linear actuator preferably comprises a stepper motor.

In a third aspect, a syringe for a syringe pump system is disclosed. The syringe comprises a plunger rod, and a plunger button coupled to the plunger rod, the plunger rod having a plunger longitudinal axis, the plunger button is configured to detachably mate with a syringe connector of a pump.

In a third preferred embodiment, the syringe preferably further comprises a syringe threaded coupler configured to detachably couple with a pump. The syringe preferably comprises a glass syringe.

In a fourth aspect, a method for using a syringe pump system is disclosed. The method comprises providing a pump, the pump comprising a linear actuator, a shaft having a shaft longitudinal axis, the shaft having a first and a second end, the first end coupled to the linear actuator, and a cylindrical syringe connector coupled to the second end of the shaft, where the cylindrical syringe connector centered about the shaft longitudinal axis, the syringe connector having a T-slot formed the outer radial surface of the syringe connector and forming a channel on the adjacent flat surface of the syringe connector extending to the radial center of the syringe connector. The method further comprises providing a syringe, the syringe comprising a plunger rod, and a plunger button coupled to the plunger rod, the plunger rod having a plunger longitudinal axis, the plunger button is configured to detachably mate with the syringe connector. The method further comprises aligning the plunger button and plunger rod to the slot on the cylindrical syringe connector, where the shaft longitudinal axis is parallel and offset with the plunger longitudinal axis. The method further comprises inserting the plunger button and the plunger rod of the syringe into the syringe connector so that the shaft longitudinal axis is coincident with the plunger longitudinal axis, and attaching the body of the pump to the body of the syringe.

In a fourth preferred embodiment, the mount block further comprises a mount block threaded coupler, and the syringe further comprises a syringe threaded coupler. Attaching the body of the pump to the body of the syringe comprises rotating the syringe threaded coupler with respect to the mount block threaded coupler to detachably couple the syringe to the pump.

These and other features and advantages of the invention will become more apparent with a description of preferred embodiments in reference to the associated drawings.

DESCRIPTION OF THE DRAWINGS

FIG. 5 is a side view of the inline pump with a rear attachable syringe.

FIG. 6 is a top, cross-sectional, perspective view of the inline pump with a rear attachable syringe.

FIG. 8 is a side view of the inline pump with a rear attachable syringe.

FIG. 9 is a front, cross-sectional view of the inline pump with a rear attachable syringe.

DETAILED DESCRIPTION OF THE PREFERRED EMBODIMENTS

One or more embodiments provide an inline pump with a rear attachable syringe. The pump and the syringe are each designed so that the pump syringe system may be easily coupled and decoupled in the field. An end mount block on the pump has a slot shaped to accept a similarly shaped plunger button and plunger rod on the syringe. A user aligns the plunger button of the syringe next to the slot on the mount block of the pump, and slides the plunger button and rod into the inner cavity of the pump. Both the pump and the syringe have threaded couplers which securely couple the pump to the syringe by rotating the couplers with respect to each other.

Figure 1:
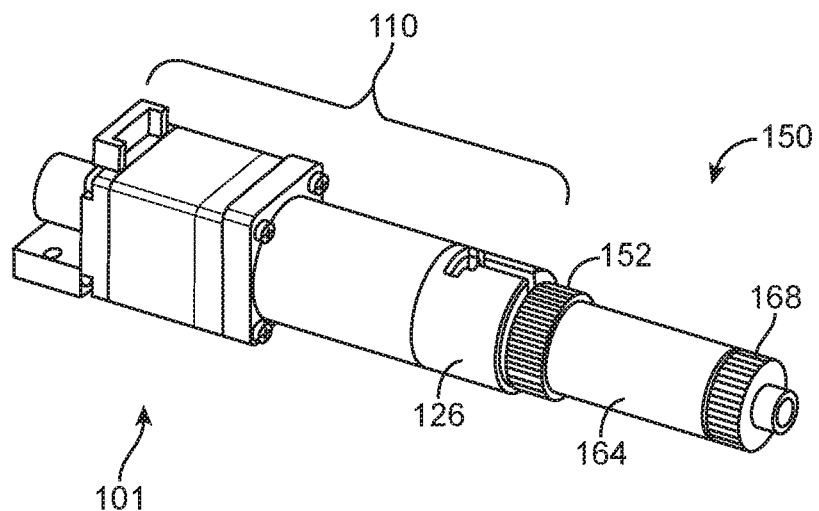
FIG. 1 is a perspective view of an inline pump with a rear attachable syringe in an embodiment.

FIG. 1 is a perspective view of an inline syringe pump system 101. The syringe pump system 101 comprises a pump 110 and a syringe 150. The pump 110 has a mount block 126 configured to couple with the syringe 150. The syringe has a syringe rear end cap 152, a syringe glass barrel 164, and a syringe front end cap 168. The syringe rear end cap 152 couples to and mates with the mount block 126 of the pump 110 to form a syringe pump system 101.

Figure 2:
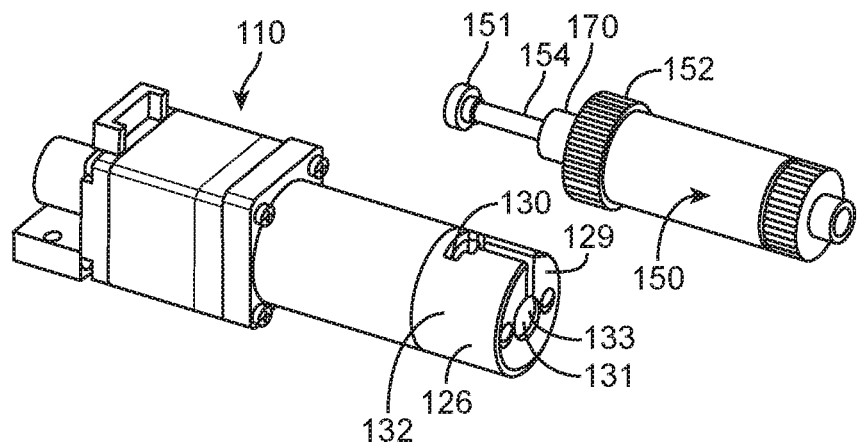
FIG. 2 is a perspective view illustrating the syringe detaching from the pump.
Figure 3:
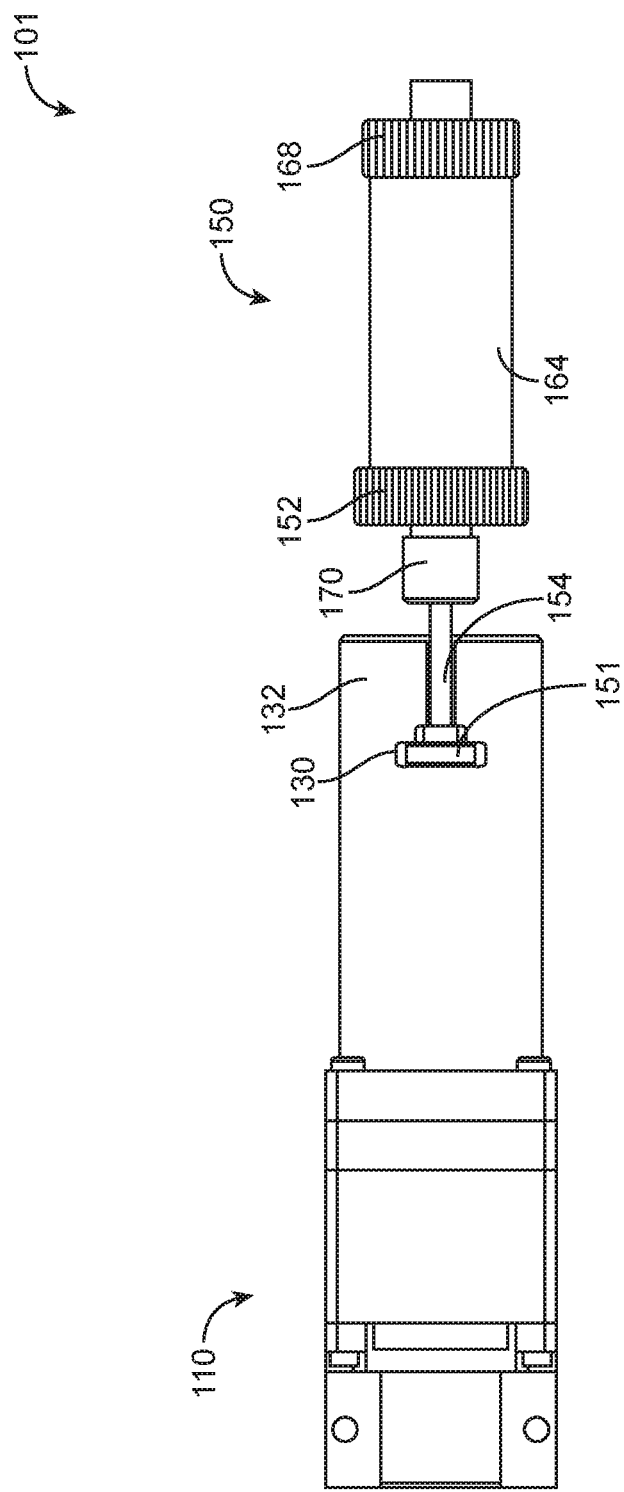
FIG. 3 is a top view of the syringe coupled to the inline pump.

FIG. 2 is a perspective view illustrating the syringe 150 detaching from the inline pump 110. The syringe 150 has a plunger rod 154 coupled to a disc-shaped plunger button 151. The syringe rear end cap 152 has a threaded region 170 to form a male threaded coupler. The mount block 126 of the pump 110 has a hole 131 with a threaded region 133 which extends through the mount block 126. The mount block 126 also has a T-slot 130 which extends from the outer radial surface 132 of the mount block 126 intersecting and extending beyond the hole 131. FIG. 3 shows the top view of the syringe pump system 101 illustrating T-slot 130 receiving the plunger rod 154 and the plunger button 151 during assembly.

As used herein, a T-slot refers to a recessed slot in the form of an inverted "T." A T-slot formed on a cylindrical part may have a wide slot formed beneath the flat surface of the cylinder which extends from the outer radial surface to beyond the inner center axis of the cylinder. A second narrower slot is formed on the flat surface to expose the wide slot. The wide slot is sized to receive the plunger button 151, and the narrow slot is sized to receive the plunger rod 154. The wide slot may extend beyond the center of the cylinder such that the plunger button 151 and plunger rod 154 have an axis coincident with axis of the hole 131.

Figure 4:
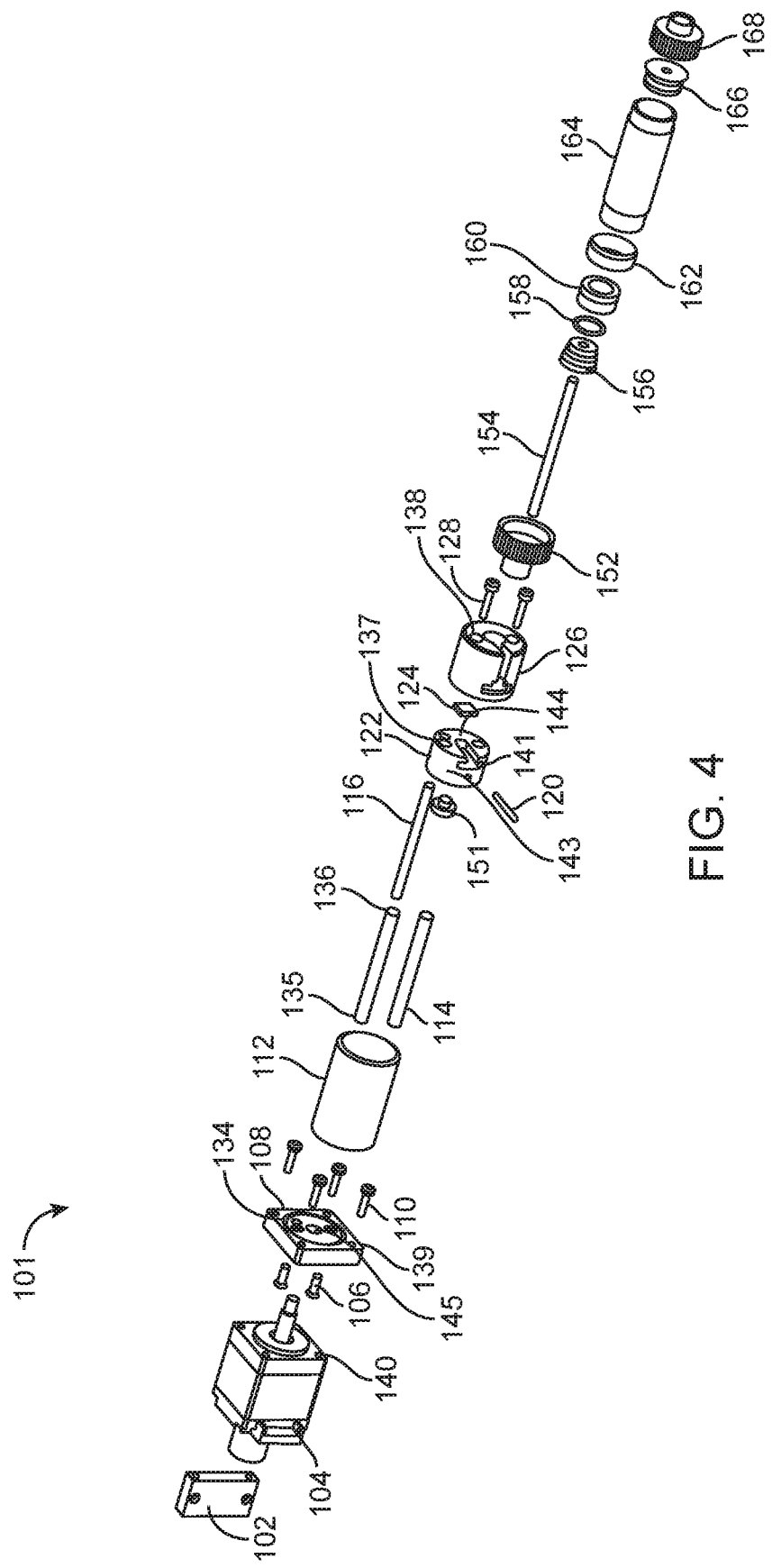
FIG. 4 is an exploded view of the inline pump with a rear attachable syringe in one or more embodiments.

FIG. 4 is a top, exploded view of the pump 110 and the syringe 150. In one or more embodiments, the pump 110 comprises an adapter bracket 102, a linear actuator 104, a guide standoff screws 106, an adapter plate 108, adapter bracket mount screws 110, an acrylic sleeve 112, guide standoffs 114, a lead screw or shaft 116, a drive pin 120, an actuator nut (i.e., a cylindrical syringe connector) 122, a micro-switch or sensor 124, a mount block 126, and front guide standoff screws 128. The linear actuator 104 has threaded holes 140 for receiving the adapter bracket mount screws 110, and a through hole 145 is formed at the center of the adapter plate 108. The actuator nut (i.e., a cylindrical syringe connector) 122 has a T-slot 141 formed on the outer radial surface 143 of the syringe connector 122 forming a channel on the adjacent flat surface 144 of the syringe connector 122 that extends to the radial center of the syringe connector 122.

In one or more embodiments, the linear actuator 104 may comprise a stepping motor having internal rotating nuts which engage with the teeth of a lead screw 116. The rotation of the stepper motor is transforming into a linear motion along the length of the lead screw 116. While a stepper motor is contemplated in one or more embodiments, it shall be understood that other types of linear actuators including, but not limited to screw, wheel and axle mechanical actuators, cam mechanical actuators, pneumatic or hydraulic actuators, linear motors, telescoping linear actuators, and other devices which provide linear motion are contemplated in one or more embodiments.

The syringe 150 comprises a syringe plunger button 151, a syringe rear end cap 152, a plunger rod 154, a syringe end plug 156, an o-ring 158, a syringe plunger tip 160, a syringe threaded sleeve 162, a syringe barrel 164, a syringe Luer tip 166, and a syringe front end cap 168. In one or more embodiments, syringe 150 comprises a glass syringe.

Figure 7:
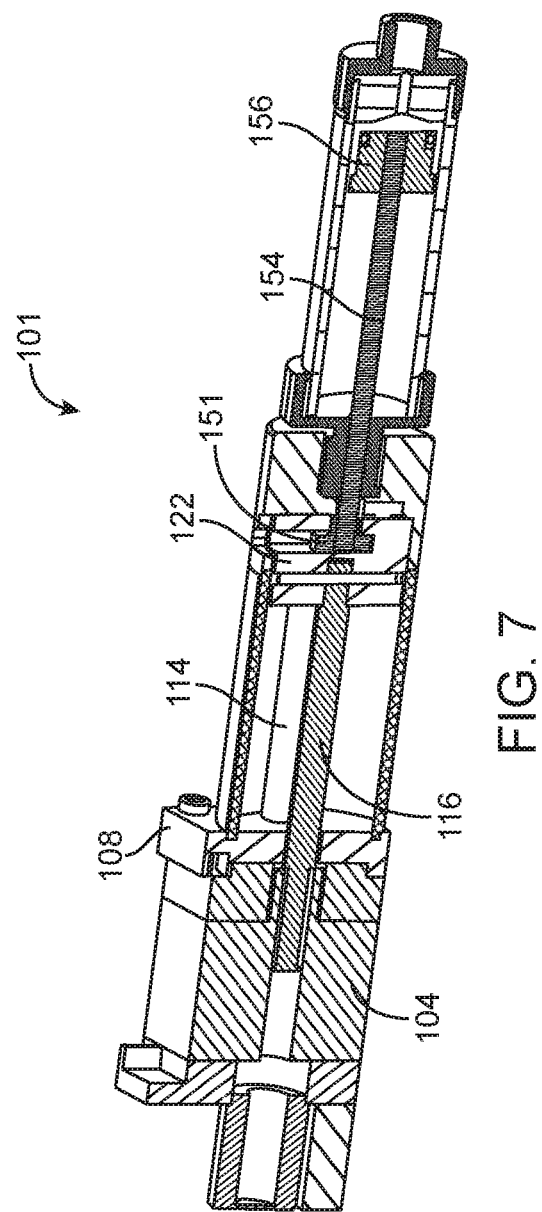
FIG. 7 is a side, cross-sectional view of the inline pump with a rear attachable syringe.

FIG. 5 is a front view of the syringe pump system 101 in an orientation where the slot 130 is at the top. FIG. 6 is the A-A cross section of the assembled syringe pump system 101. FIG. 7 is a perspective view of the A-A cross section of the assembled syringe pump system 101. In an embodiment, the pump 110 comprises a linear actuator 104, a shaft (i.e., a lead screw) 116 having a shaft longitudinal axis 148. The shaft has a first end 117a and a second end 117b, where the first end 117a is coupled to the linear actuator 104. The cylindrical syringe connector 122 (i.e. actuator nut) is coupled to the second end of the shaft 117b. The syringe 150 comprises a syringe plunger rod 154 which has a plunger longitudinal axis 180. The syringe 150 also comprises a plunger button 151 coupled to the plunger rod 154, where the plunger button 151 is configured to detachably mate with the syringe connector 122. In one or more embodiments, the shaft longitudinal axis 148 is coincident with the plunger longitudinal axis 180. In an embodiment, the plunger button 151 comprises a cylindrical disc radially extending away from the plunger rod 154.

The cylindrical syringe connector 122 (i.e., actuator nut) is centered about the shaft longitudinal axis 148. As shown in FIG. 4, the syringe connector 122 has a T-slot 141 formed on the outer radial surface 143 of the syringe connector 122 and forming a channel on the adjacent flat surface 144 of the syringe connector 122 extending to the radial center of the syringe connector 122. The cylindrical syringe connector 122 is configured to receive the plunger button 151 and the plunger rod 154 and align the plunger longitudinal axis 148 coincident with the shaft longitudinal axis 180.

As shown in FIG. 2, the pump 110 further comprises a mount block 126 at an end of the pump 110. The mount block 126 has a mount block T-slot 130 formed the outer radial surface 132 of the mount block 126 which forms a channel on the outer flat surface 129 of the mount block 126 that extends to the radial center of the mount block 126, such that the mount block 126 is configured to align with the syringe connector 122 and receive the plunger button 151 during assembly.

In one or more embodiments, the mount block 126 has a threaded region 133 to form a mount block threaded coupler. The syringe 150 further comprises a threaded region 170 to form a syringe threaded coupler. The mount block 133 threaded coupler is configured to receive and mate with the syringe threaded coupler 170 to detachably connect the syringe 150 to the pump 110.

The linear actuator 104 is coupled to the lead screw 116 (i.e. a shaft), which is, in turn, connected to the actuator nut 122 (i.e. a cylindrical syringe connector) via the drive pin 120. The actuator nut 122 cradles the syringe plunger button 151. The syringe plunger button 151 is connected to the plunger rod 154, which is, in turn, connected to the syringe end plug 156. FIGS. 6 and 7 depict a scenario in which the syringe pump system 101 is fully in a forward dispense position.

To begin an aspiration cycle, the linear actuator 104 engages with the lead screw 116 by applying force to the lead screw 116 and pulling the lead screw 116 to the left and within the body of the lead actuator 104. As the lead screw 116 is indirectly coupled to the plunger rod 154, the syringe end plug 156 will also move to the left drawing a liquid into the syringe front end cap 168.

To begin a dispense cycle, the linear actuator 104 engages with the lead screw 116 by applying force to the lead screw 116 pushing the lead screw 116 to the right. As the lead screw 116 is indirectly coupled to the plunger rod 154, the syringe end plug 156 will also move to the right dispensing liquid out of the syringe front end cap 168.

In one or more embodiments, a micro-switch or sensor 124 coupled to the mount block 126 is configured to detect the immediate presence of the syringe connector 122. When the syringe connector 122 is adjacent to the mount block 126, the sensor 124 notifies the linear actuator control board (not shown) to stop the forward motion of the syringe connector 122.

FIG. 8 is a front view of the syringe pump system 101 in an orientation where the slot 130 is at the side. FIG. 9 is the B-B cross section of the assembled syringe pump system 101. An adapter plate 108 is mounted to the linear actuator 104, and the adapter plate 108 has an adapter plate through hole 145 coincident with the shaft longitudinal axis 148 as shown in FIG. 4. The pump 110 has two guide standoffs 114 which couple the mount block 126 to the adapter plate 108. Guide standoff screws 106 are placed in through holes 134 in the adapter plate 108 and are connected to the threaded holes 135 in the guide standoffs 114. Adapter bracket mount screws 110 are placed in the through holes 139 on the adapter plate 108 and are connected to the threaded holes 140 on the linear actuator 140. Guide standoff screws 128 are placed into the through holes 137 of the actuator nut 122 and are connected to the threaded holes 136 of the guide standoffs 114. As a result, the actuator nut 122 does not rotate about the lead screw 116, but the actuator nut is movable along the longitudinal axis defined by the length of the lead screw 116.

Figure 10:
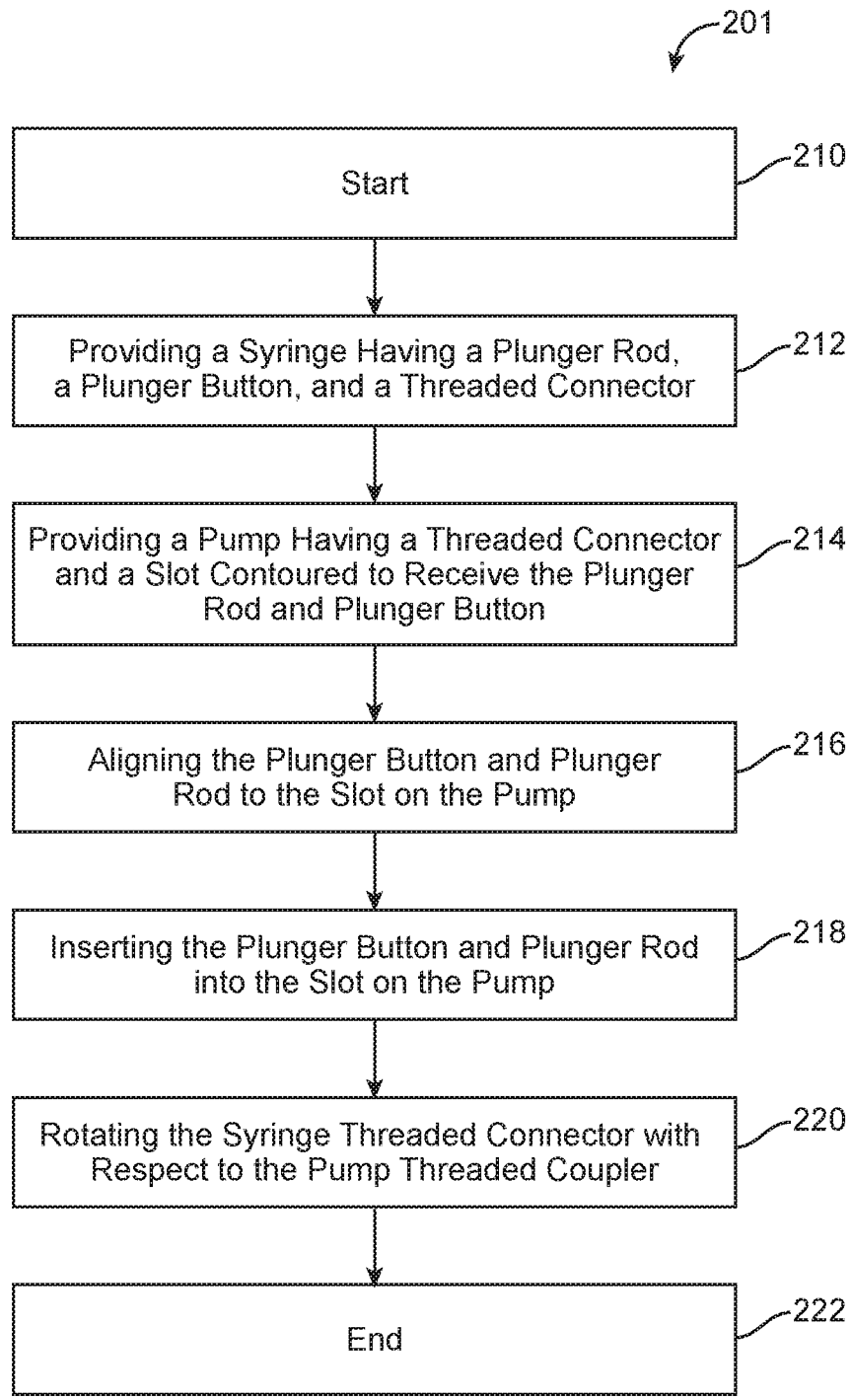
FIG. 10 presents an exemplary process for connecting the syringe to the pump in one or more embodiments.

FIG. 10 presents an exemplary process 201 for connecting the syringe 150 to the pump 110. The process begins (step 210) by providing a syringe 150 (step 212). The syringe 150 comprises a plunger rod 154 and a plunger button 151 coupled to the plunger rod 143. The plunger rod 154 has a plunger longitudinal axis 180. The plunger button 151 is configured to detachably mate with the syringe connector 122.

A pump is provided (step 214). The pump comprises a linear actuator 104 and a shaft 116 having a shaft longitudinal axis 148. The shaft has a first end 117a and a second end 117b, where the first end 117a is coupled to the linear actuator 104. The pump 110 further comprises a cylindrical syringe connector 122 coupled to the second end 117b of the shaft, where the cylindrical syringe connector 122 is centered about the shaft longitudinal axis 148. The syringe connector 122 has a T-slot 141 formed the outer radial surface 143 of the syringe connector 122 which forms a channel on the adjacent flat surface 144 of the syringe connector 122 that extends to the radial center of the syringe connector.

The plunger button 151 and plunger rod 154 are aligned to the slot 141 on the cylindrical syringe connector, where the shaft longitudinal axis 148 is parallel and offset with the plunger longitudinal axis 180 (step 216). The plunger button 151 and the plunger rod 154 of the syringe 150 are inserted into the syringe connector 122 so that the shaft longitudinal axis 148 is coincident with the plunger longitudinal axis 180 (step 218). The body of the pump to the body of the syringe is rotated with respect to the pump to detachably couple the syringe to the pump (step 220). The process ends (step 222).

Several features of syringe pump system 101 are notable. One significant feature of the syringe pump system 150 is the rear mount on the syringe 150. This eliminates the need for a manifold or an expensive cartridge. This allows the use of a traditional glass barrel syringe with plunger tip to replace the positive displacement syringe. This results in fewer parts, cost reduction, simplicity of assembly and simplicity of changing the syringe. A shorter fluid path (with less internal volume) is another feature. The dead volume inside the syringe 150 is virtually eliminated. In one or more embodiments, the shorter fluid path may be one of the key components of this design. A typical pump (with interchangeable syringe) is screwed into a manifold at the top of the pump and driven with a "fixed" connection to the driver pin of the pump at the bottom. This manifold with its internal volume is eliminated. The line fitting screws into the port on the top of the syringe. Ease of changing the syringe, cost reduction, reduced internal volume and the "floating" plunger button may be all benefits in a preferred embodiment.

An additional feature incorporates the guide standoffs 114 which prevent rotation of the drive nut 122—a necessary feature to provide linear travel for aspirate and dispense. In addition to this standard function, they form the framework of the pump 110 eliminating the need for a rigid frame. This lowers assembly time with fewer parts to reduce costs.

A third feature is the "quick change" plunger button 151/actuator nut 122 interface. This allows the plunger button 151 to "float" laterally in the actuator nut 122, while providing virtually "back lash free" linear motion. This feature eliminates "side load" and resulting wear on the guide of the rear end cap.

The problem of the difficulty in changing the syringe such as to field service a syringe or switch to a different volume syringe is also addressed. In this in-line pump 110, the syringe 150 is integrally imbedded in the pump 150. Simply send pump 110 to full dispense, unscrew the syringe 150 and slide out laterally.

Another problem related to the assembly of the pump unit is also addressed. Optical sensors or "crash and dash" stops are undesirable. The home position is built into the pump and no additional settings are needed to change out a syringe.

In addition, assembly of the syringe pump system 101 is accomplished by simply bolting the standoff/guides in front and rear position and all positioning settings and additional parts are eliminated. The micro-switch 124 prevents over travel crashes and does not need to be reset. Select linear tolerance controls eliminate all home position settings.

The problem associated with excessive side load is also addressed. This excessively wears the plunger rod and increased load could cause the stepper motor to lose steps. The resulting stepper moves would result in "short dispenses" or over travel crashes. The floating plunger button 151 eliminates this.

One purpose of the syringe pump system 101 is to provide an "easy to use" low cost alternative to existing pumps utilizing features sought by customers, which are not included on existing in line pumps.

Among the potential benefits offered by one or more embodiments may include eliminating complicated and time consuming assembly, eliminating assembly and in the field home positioning procedures, offering different volume syringes that are easily interchangeable and cost effective, providing the smallest footprint available in an in line pump, and eliminating side load alignment issues. Syringes may have traditionally been mounted from the front. A rear mount offers opportunities to devise new quick change features. Moreover, having a fixed micro-switch 124 controlled by select tolerance controls offered and opportunity to create a new design. In addition, using standoffs to do multi-function tasks (guiding and provide a frame for the pump) opened new design possibilities. These features may provide reduced costs by 50%, reduced side load wear by 50%, reduced assembly time by 60%, improved precision and accuracy by 25% due to reduced side load, reduced power requirements due to reduced friction by 20%, reduced syringe changeover time 60%, and improved field serviceability by 80%.

One or more embodiments of the syringe pump systems 101 could be used for "pre-packaged" serum or sample dispense. Pumps 110 and syringes 150 are easily adaptable to robotics and automation. Components are designed to be easily reproduced by molding, 3-D printing, stamping, and forming.

The syringe pump system 101 may offer several features for unique design and cost effectiveness. First, the syringe has a threaded rear end cap on the back end of the syringe 150. This rear threaded end cap may be unique among conventional syringes and may be unique for use in an in line pump. This design eliminates the manifold entirely which may reduce costs. It gives the option to easily change the size of the syringe or replace an existing defective syringe. In one or more embodiments, changing the syringe 150 does not require that the pump 110 to be dissembled, thus avoiding exposing sealing areas which may otherwise placing the fluidic integrity of the pump assembly at risk.

Second, the fluidic fitting port to transport the media is directly on the front end cap on the front of the syringe 150 with a ¼-28 or M6 fitting (or to customer specifications). This allows easy connection to the fluidic system of the customer. The mating fitting screws directly into the syringe.

Third, the design incorporates unique guide stand-offs 114. Besides providing "non-rotation" for the actuator nut 122 which is necessary for the linear motion of the linear stepper motor, the guide standoffs 114 also form the framework of the pump 110. This provides ease of assembly and the cost reduction of eliminating the rigid frame to which the guide is usually attached. This also eliminates many of the in line alignment issues.

Assembly of the syringe pump system 101 is accomplished through the insertion and removal of the syringe. First, the syringe plunger button 151 is pulled backward about halfway. Second, with the pump 110 in the full forward dispense position, the plunger button 151 is slid through the mount 126 and into the mating slot in the actuator nut 122. The guide on the rear end cap keeps the plunger rod 154 "in line" and the unique "floating action" between the plunger button and the actuator nut prevents "side load" on the plunger rod. This prevents excess wear and loss of accuracy and precision through increased side load. Each time the pump 110 goes through the aspirate/dispense cycle, the syringe realigns itself.

Third, the syringe 150 is then pushed downward until the threaded portion of the rear end cap contacts the female thread on the mount block. The syringe is then threaded down hand tight until it bottoms out and the installation is complete.

A unique feature may be that the absence of "home position" setting. Typical home position is set by an adjustable optical sensor. This pump utilizes high tolerances on key linear dimensions and a fixed micro switch. This allows easy interchange for a worn syringe or changing to a different size. The "home position" is basically the position that is used to orient the syringe to the pump so that a full stroke is achieved. Typically an optical sensor with a linear sliding bracket to "tell" the pump where it is at when the syringe is fully forward so that no more fluid can be dispensed. In one or more embodiments, a micro-switch is imbedded (epoxy potted) in the mount block and would come in contact at "full dispense" with the actuator nut. A millivolt signal would then be instantaneously sent to the driver board, telling the stepper to stop, and then reverse direction a certain number of steps, enough to disengage the micro-switch such as 20 steps. The key dimensions are built into the plunger and glass barrel assemblies, actuator nut, and mount block to insure interchangeability between all replacement syringes, whether change for wear issues or to change to a different volume syringe To remove the syringe 150, once again move the pump 110 to full forward and reverse the installation procedure. "Y" connectors (or a single fluidic connector) will fit into the front end cap of the syringe to utilize check valves or other aspirate/dispense valves.

Typical syringe sizes would be 100 µL, 250 µL, 500 µL, 1 ML, 2.5 ML and 5 ML only by changing the syringe size. Of course, the amount each syringe dispenses is controlled by the amount of steps programmed into the stepper motor. Steps per second are programmed in to change flow rate.

Although the invention has been discussed with reference to specific embodiments, it is apparent and should be understood that the concept can be otherwise embodied to achieve the advantages discussed. The preferred embodiments above have been described primarily as inline pumps with rear attachable syringes. In this regard, the foregoing description of the inline syringe pump systems is presented for purposes of illustration and description. Furthermore, the description is not intended to limit the invention to the form disclosed herein. Accordingly, variants and modifications consistent with the following teachings, skill, and knowledge of the relevant art, are within the scope of the present invention. The embodiments described herein are further intended to explain modes known for practicing the invention disclosed herewith and to enable others skilled in the art to utilize the invention in equivalent, or alternative embodiments and with various modifications considered necessary by the particular application(s) or use(s) of the present invention.

What is claimed is:

1. A pump for a syringe pump system, the pump comprising:
    a linear actuator;
    a shaft having a shaft longitudinal axis, the shaft having a first and a second end, the first end coupled to the linear actuator;
    a cylindrical syringe connector coupled to the second end of the shaft, the cylindrical syringe connector configured to detachably mate with a plunger button of a syringe, and the cylindrical syringe connector further configured to position the shaft longitudinal axis coincident with a plunger longitudinal axis of a plunger rod of the syringe when the cylindrical syringe connector is mated with the plunger button of the syringe;
    an adapter plate mounted to the linear actuator, the adapter plate having an adapter plate through hole coincident with the shaft longitudinal axis; and
    a pair of guide stand-offs affixed to the adapter plate and passing into holes in the syringe connector, wherein the pair of guide stand-offs are disposed to prevent the syringe connector from rotating about the shaft.

2. The pump for the syringe pump system of claim 1, wherein the cylindrical syringe connector is centered about the shaft longitudinal axis, the syringe connector having a T-slot formed in the outer radial surface of the syringe connector forming a channel on the adjacent flat surface of the syringe connector extending to the radial center of the syringe connector;
    wherein the cylindrical syringe connector is configured to receive the plunger button and the plunger rod of a syringe and align the plunger longitudinal axis coincident with the shaft longitudinal axis.

3. The pump for the syringe pump system of claim 1, wherein the pump further comprises a mount block at an end of the pump, the mount block having a mount block T-slot formed in the outer radial surface of the mount block and forming a channel on an outer flat surface of the mount block extending to the radial center of the mount block, wherein the mount block is configured to align with the syringe connector and receive the plunger button when the cylindrical syringe connector is mated with the plunger button of the syringe.

4. The pump for the syringe pump system of claim 3, wherein the mount block further comprises a mount block threaded coupler.

5. The pump for the syringe pump system of claim 1, wherein the pair of guide stand-offs is coupled to a mount block at an end of the pump, the mount block having a mount block T-slot formed an outer radial surface of the mount block and forming a channel on the outer flat surface of the mount block extending to the radial center of the mount block, wherein the mount block is configured to align with the syringe connector and receive the plunger button when the cylindrical syringe connector is mated with the plunger button of the syringe.

6. The pump for the syringe pump system of claim 1, wherein the pump further comprises a micro-switch configured to detect the presence of the syringe connector.

7. The pump for the syringe pump system of claim 1, wherein the linear actuator comprises a stepper motor.

8. A syringe pump system, the system comprising:
    a pump comprising:
    a linear actuator;
    a shaft having a shaft longitudinal axis, the shaft having a first and a second end, the first end coupled to the linear actuator,
    a cylindrical syringe connector coupled to the second end of the shaft,
    a mount block disposed at an end of the pump,
    an adapter plate mounted to the linear actuator, the adapter plate having an adapter plate through hole coincident with the shaft longitudinal axis, and
    a plurality of guide stand-offs, each guide stand-off coupled to the adapter plate, passing through guide through holes on the syringe connector, and coupled to the mounting plate, wherein the guide stand-offs prevent the syringe connector from rotating about the shaft; and
    a syringe comprising:
    a plunger rod, the plunger rod having a plunger longitudinal axis, and
    a plunger button coupled to the plunger rod.

9. The syringe pump system of claim 8, wherein the shaft longitudinal axis is coincident with the plunger longitudinal axis.

10. The syringe pump system of claim 8, wherein:
    the plunger button comprises a cylindrical disc radially extending away from the plunger rod; and,
    the cylindrical syringe connector is centered about the shaft longitudinal axis, the syringe connector having a T-slot formed in an outer radial surface of the syringe connector forming a channel on a forward-facing surface circumscribed by the outer radial surface of the syringe connector, the channel extending to the radial center of the syringe connector;

wherein the T-slot on the cylindrical syringe connector is configured to receive the plunger button and the plunger rod and align the plunger longitudinal axis coincident with the shaft longitudinal axis.

11. The syringe pump system of claim 8, wherein the mount block includes a mount block T-slot formed in the outer radial surface of the mount block and forming a channel on an outer flat surface of the mount block extending to the radial center of the mount block, wherein the mount block is configured to align with the syringe connector and receive the plunger button during assembly.

12. The syringe pump system of claim 8, wherein:
the mount block further comprises a mount block threaded coupler; and,
the syringe further comprises a syringe threaded coupler;
wherein the mount block threaded coupler is configured to receive and mate with the syringe threaded coupler to detachably connect the syringe to the pump.

13. The syringe pump system of claim 8, wherein the plunger button is configured to detachably mate with the plunger rod.

14. The syringe pump system of claim 8, wherein the linear actuator comprises a stepper motor.

15. The syringe pump system of claim 8, wherein the syringe comprises a glass syringe.

16. The syringe pump system of claim 8, wherein the pump further comprises a sleeve, wherein the sleeve surrounds the cylindrical syringe connector.

17. A pump for a syringe pump system, the pump comprising:

a linear actuator;

a shaft having a shaft longitudinal axis, the shaft having a first and a second end, the first end coupled to the linear actuator;

a cylindrical syringe connector coupled to the second end of the shaft, the cylindrical syringe connector configured to detachably mate with a plunger button of a syringe, and position the shaft longitudinal axis coincident with a plunger longitudinal axis of a plunger rod;

an adapter plate mounted to the linear actuator, the adapter plate having an adapter plate through hole coincident with the shaft longitudinal axis;

a mount block at an end of the pump; and a plurality of guide stand-offs, each guide stand-off coupled to the adapter plate, each guide stand-off passing through respective guide through holes on the syringe connector, and each guide stand-off passing into respective through holes of the mount block, wherein the guide stand-offs prevent the syringe connector from rotating about the shaft.

18. The pump for the syringe pump system of claim 17, wherein the mount block is configured to align with the syringe connector and receive the plunger button when the cylindrical syringe connector is mated with the plunger button of the syringe.

19. The pump for the syringe pump system of claim 17, wherein the mount block further comprises a mount block threaded coupler.

20. The pump for the syringe pump system of claim 17, wherein the cylindrical syringe connector is configured to receive the plunger button and the plunger rod of a syringe and align the plunger longitudinal axis coincident with the shaft longitudinal axis.

\* \* \* \* \*